(12) United States Patent
David et al.

(10) Patent No.: US 7,647,839 B2
(45) Date of Patent: Jan. 19, 2010

(54) INSTALLATION AND METHOD FOR TESTING SYSTEM OF LOADS OF A SAMPLE USING A PACKER

(75) Inventors: Didier David, Ruesnes (FR); Thierry Noel, Sebourg (FR); Gabriel Roussie, Cappelle en Pévèle (FR)

(73) Assignee: Vallourec Mannesmann Oil & Gas France, Aulnoye-Aymeries (FR)

( * ) Notice: Subject to any disclaimer, the term of this patent is extended or adjusted under 35 U.S.C. 154(b) by 214 days.

(21) Appl. No.: 11/816,532

(22) PCT Filed: Feb. 23, 2006

(86) PCT No.: PCT/FR2006/000410

§ 371 (c)(1),
(2), (4) Date: Oct. 9, 2007

(87) PCT Pub. No.: WO2006/095070

PCT Pub. Date: Sep. 14, 2006

(65) Prior Publication Data

US 2008/0264632 A1   Oct. 30, 2008

(30) Foreign Application Priority Data

Mar. 4, 2005 (FR) .................................. 05 02207

(51) Int. Cl.
*G01N 3/00* (2006.01)
(52) U.S. Cl. .......................................... 73/807; 73/760
(58) Field of Classification Search ............ 73/760–860
See application file for complete search history.

(56) References Cited

U.S. PATENT DOCUMENTS

| 3,787,226 | A | * | 1/1974 | Iglehart et al. | ............... 427/235 |
| 4,067,349 | A | * | 1/1978 | Austin et al. | .................... 38/97 |
| 4,416,147 | A | | 11/1983 | Hasha | |
| 4,899,588 | A | * | 2/1990 | Titlow et al. | .................. 73/597 |
| 6,161,425 | A | | 12/2000 | Junker et al. | |
| 6,772,839 | B1 | * | 8/2004 | Bond | .......................... 166/298 |

FOREIGN PATENT DOCUMENTS

| DE | 38 27 080 | 2/1990 |
| FR | 2 564 973 | 11/1985 |
| FR | 2 618 901 | 2/1989 |

* cited by examiner

*Primary Examiner*—Max Noori
(74) *Attorney, Agent, or Firm*—Oblon, Spivak, McClelland, Maier & Neustadt, L.L.P.

(57) ABSTRACT

A unit dedicated to mechanically loading a tubular sample. At least one packer is housed in a sample at a test zone, having a longitudinal extension greater than that of the test zone and including i) a first pressure mechanism to cause local variation in the diameter of at least a first portion of the packer so as to apply the packer against an internal surface of the sample at the test zone, ii) a second pressure mechanism exerting a first selected internal pressure over a portion of the internal surface located at a second portion of the packer, and/or iii) a third pressure mechanism to cooperate with at least one plug member attached to the sample at a distance from one end of the packer to define a zone of action, to exert on the sample a second selected internal pressure at the zone of action.

48 Claims, 4 Drawing Sheets

FIG.1

KEY

| | | |
|---|---|---|
| Mesure de fréquence | = | frequency measurement |
| 16 voies d'entrées AC | = | 16 AC input channels |
| Mesures accélérométriques | = | Accelerometric measurements |
| Adaptation 24V | = | 24V conversion |
| Comptage de cycles | = | cycle counting |
| 16 voies d'entrées DC | = | 16 DC input channels |
| 1 sortie DC consigne variateur | = | 1 DC output, reference variable, variator |

INSTALLATION AND METHOD FOR TESTING SYSTEM OF LOADS OF A SAMPLE USING A PACKER

The invention concerns mechanical loading tests for tubular samples.

The term "tubular sample" as used here means any tube or assembly of tubes which are connected together, possibly via a coupling. As a result, it may be either a single tube or two tubes connected by any means, for example by welding, or two tubes respectively comprising male and female threadings connected via a threaded connection constituted by said male and female threadings made up one into each other, or two tubes each provided with a male threading and connected to each other via a threaded connection constituted by a coupling provided with two female threadings.

Further, the term "tube" as used here means any tubular component intended to be used in a difficult operational environment as regards pressure and/or mechanical loads and/or corrosion and/or temperature, such as an oil well or a refinery. It may thus, for example, concern a drill pipe or a smooth or threaded weld-less tube for a casing or for the production of oil or gas (tubing), or a line, or a pipeline.

In order to represent behaviour equivalent to various combinations of static loads imposed on a tubular sample, the skilled person normally uses a Von Mises ellipse the two principal axes of which are respectively representative of an axial load and the pressure undergone by said sample, said axial load possibly comprising compression, tension or bending.

To test the behaviour of tubular samples in the laboratory under combinations of loads, the skilled person uses a unit comprising a load bench (termed a fatigue bench when it produces dynamic loads) and observes the behaviour of said combinations of loads using a Von Mises ellipse.

First examples of known static load units which may be cited are those which consist of introducing a pressurized fluid into a tubular sample the ends of which have been attached to plugs, and second examples are those which consist of using a jack placed inside or outside a tubular sample; third examples are those which consist of combining the first two types.

In the type of unit using an internal pressurized fluid, the tubular sample undergoes both tension and pressure. This results from the fact that the internal pressurized fluid induces not only a pressure (essentially radial) on the internal wall of the tubular sample, but also pressure (essentially axial) on the plug means at the end which induces an axial tension on the tubular sample. Since the intensity of the pressure is proportional to the pressure, when the pressure is varied, the tension is thus varied in the same proportions. That type of unit thus prohibits a study of the influence of pressure independently of the influence of tension. That type of unit thus cannot explore any combination of pressure and axial tension, but only a combination which can be modeled by a segment of the major axis of the Von Mises ellipse.

In the type of unit using an internal or external jack, the tubular sample undergoes only axial tension. That type of unit thus prohibits a study of the influence of pressure alone, and also a study of any combination of pressure and axial tension, but only a combination which can be modelled by a segment of the abscissa (X) of the plane representing the Von Mises ellipse.

A unit using both a jack and an internal pressurized fluid allows at least a portion of the plane of representation of the Von Mises ellipse to be described, but at the cost of a complicated unit.

Further, the units presented above can only be used to load the samples in a static manner. However, that type of load cannot reproduce certain difficult operational conditions which also impose dynamic loads, for example those encountered in structures composed of tubes and connections which link an offshore platform to the head of a well which may be located several kilometers away, or those encountered by similar structures in deviated wells necessitating rotation of the string. Such structures are subjected to cyclic bending loads, which may be superimposed on the internal static pressure and/or axial tensional loads. A unit which is also termed a fatigue bench is then used to test samples in dynamic loads.

Thus, the invention aims to propose an alternative to static units which use a jack and pressurized fluid at the same time, and optionally to test samples in a dynamic manner.

To this end, it proposes a unit for mechanically loading a tubular sample, comprising at least one packer housed in the sample at a test zone, having a longitudinal extension which is greater than that of the test zone and comprising, firstly, first pressure means for locally varying the diameter of at least a first portion of the packer to apply it against an internal surface of the sample at the test zone, and secondly, second pressure means instructed to exert a first selected internal pressure over a portion of the internal surface of the sample, located at a second portion of the packer, and/or thirdly, third pressure means instructed to cooperate with at least one plug member, attached to the sample at a distance from one end of the packer to define a zone of action in which the sample undergoes a second selected internal pressure, which is independent of the first pressure.

The unit of the invention may include complementary characteristics which may be taken separately or in combination, in particular:

- at least one strain gauge is placed at a selected region of the external surface of the sample, delivering first stress measurements representative of a stress state undergone by the sample at the selected region;
- at least two strain gauges are placed in two different selected regions of the external surface and delivering first stress measurements representative of the stress state undergone by the sample at the two selected regions;
- the desired strain by bending corresponds, for example, to initial first reference measurements;
- two support means intended to support the sample, a rotary motor is coupled to an excitation means provided with a device with an eccentric mass coupled to one end of the sample and defining an unbalanced mass, and control means instructed to order rotation of the eccentric mass by the motor at an adjustable rate, to subject the sample to a selected vibratory excitation which is a function of the unbalanced mass, to cyclically deform it by bending;
- at least one of the support means may be arranged so that its position (or their respective positions) substantially correspond to one (or more) vibration node(s) of the sample;
- the control means may then be instructed to adapt the rotary speed of the motor as a function of the amplitude of a stress representative of the bending stress to which the sample is to be subjected;
- at least one pair of accelerometers is placed at 90° to each other in selected regions of the external surface of the sample and delivers second measurements representative of a displacement to which said sample is subjected. In this case, the control means are instructed to adapt the rotary speed of the motor as a function of last second measurements delivered by the pair of accelerometers, so that the amplitude of the radial displacement by bending undergone by the sample at a selected region remains substantially constant;

at least two other pairs of accelerometers are provided. In this case, the accelerometers of each other pair are placed at 90° to each other in other selected regions of the external surface of the sample and deliver other second measurements taken at the selected other regions and representative of displacements undergone by said sample at the selected other regions. The control means may then be intended to produce combinations of the last second measurements to adapt the rate of rotation of the motor as a function of said combinations, so that the amplitude of the displacement by bending undergone by the sample at the selected regions remains substantially constant;

when the tubular sample is constituted by at least two tubular components connected together at the test zone, two pairs of accelerometers are preferably placed on both sides of the connection;

the control means may be intended to compare at least the last second measurements delivered by at least one of the pairs of accelerometers with second reference measurements representative of an initial displacement amplitude corresponding to a desired bending displacement amplitude at the selected region, then to adapt the rate of rotation of the motor as a function of the result of the comparison;

the control means may be instructed to determine a relative difference between the displacement amplitude (represented by the last second measurements) and the desired bending displacement amplitude, then to compare this difference with the limits of a "regulation" tolerance interval, to adapt the rate of rotation of the motor when the difference is outside said regulation interval;

a device for detecting rotation (or revolutions or cycles) is instructed to detect each rotation (or revolution or cycle) imposed by the motor;

said rotation detection device is, for example, instructed to send to the control means a signal representative of each detected rotation, so that they adapt the rotation rate of the motor each time the number of signals received is equal to a selected number;

the control means may be instructed to order the motor, during a loading test, to drive the eccentric mass in rotation in accordance with a selected sequence of rotation rates to subject the sample to a selected sequence of vibratory excitations;

the packer may comprise a substantially non deformable support on which a deformable annular membrane is mounted. In this case, the first pressure means comprise a first fluid supply circuit instructed to introduce a selected fluid (for example a pressurized liquid) between the substantially non deformable support and the membrane to apply a selected pressure;

the second pressure means may comprise a second circuit for supplying a fluid (for example a gas) comprising a fluid output opening facing the internal surface of the sample to apply the selected first internal pressure;

said second fluid supply circuit may, for example, traverse the membrane in a sealed manner;

leak detection means are placed close to the external surface of the sample in the test zone and are instructed to detect any leaks of fluid (delivered via the second supply circuit) at the periphery of the sample;

the third pressure means may comprise a third fluid supply circuit suitable to supply each zone of action with fluid (for example a pressurized liquid) to exert the selected second internal pressure on the sample;

a routing device is connected to the first and third fluid supply circuits, and a pump is coupled to the routing device;

the packer support is, for example, a tube forming a hollow central conduit which defines a portion of the third fluid supply circuit and which comprises two opposed ends at least one of which opens into a zone of action to supply it with fluid;

two plug members are installed at a distance from the two ends of the packer to define at least one zone of action in which the sample undergoes the selected second internal pressure;

a portion of the first fluid supply circuit and/or a portion of the second fluid supply circuit may be housed inside a central conduit;

at least one temperature sensor is installed at a selected region of the sample and delivers third measurements representative of the temperature of the sample at said selected region;

at least one pressure sensor is intended to be installed at a selected region of the sample and delivers fourth measurements representative of the internal pressure of the sample at said selected region;

control means may be instructed to compare first results derived from at least some of the first measurements with second results derived from at least some of the second measurements, to authorize continuation of the test when the first results are compatible with the second results.

The invention also concerns a process for mechanically loading a tubular sample, consisting of introducing into the sample, at a test zone, at least one packer having a longitudinal extension which is greater than that of the test zone and comprising first and second and/or third pressure means, then locally varying the diameter of at least a first portion of the packer with the first pressure means to apply said packer against an internal surface of the sample, at the test zone, and to exert with the second pressure means a first selected internal pressure over a portion of the internal surface located at a second portion of the packer, and/or to attach at least one plug member to the sample at a distance from one end of the packer to define a zone of action, then to exert a second selected internal pressure at the zone of action on the sample with the third pressure means.

The process of the invention may comprise complementary characteristics which may be taken separately or in combination, in particular:

at least one strain gauge may be used, placed at a selected region of the external surface of the sample, to obtain first stress measurements representative of the stress state undergone by the sample at the selected region;

at least two strain gauges may be used, placed in two different selected regions of the external surface, to obtain first stress measurements representative of the stress state undergone by the sample at the two selected regions;

two support means may be used on which the sample is installed, and a rotary motor coupled to an excitation means, equipped with a device with an eccentric mass coupled to one end of the sample and defining an unbalanced mass, and the eccentric mass may be driven in rotation using the motor, at an adjustable rate, so as to subject the sample to a selected vibratory excitation, which is a function of the unbalanced mass, to deform it cyclically by bending;

at least one of the support means may be placed substantially at one vibration node of the sample;

a preliminary reference step may be provided in which the initial rotation rate of the motor is initially selected as a function of the amplitude of a stress which is to be undergone by said sample;

after the preliminary reference step, the rotation rate of the motor may be adapted so that the amplitude of the bending stress undergone by the sample and represented by first measurements remains substantially constant;

at least one pair of accelerometers may be used, placed at 90° to each other at selected regions of the external surface of the sample to obtain second measurements representative of the displacement undergone by said sample. In this case, the rotation rate of the motor is adapted as a function of last second measurements delivered by the pair of accelerometers, such that the amplitude of the radial displacement by bending undergone by the sample at the selected region remains substantially constant;

it is also possible to use two other pairs of accelerometers. In this case, the accelerometers of each other pair are also placed at 90° to each other at other selected regions of the external surface of the sample and deliver other second measurements representative of the displacements undergone by the sample at the other selected regions. Combinations of last second measurements may then be made to adapt the rotation rate of the motor as a function of these combinations, such that the amplitude of the bending displacement undergone by the sample at the selected regions remains substantially constant;

at least the last second measurements delivered by at least one pair of accelerometers may be compared with second reference measurements representative of an initial displacement amplitude corresponding to a desired bending displacement amplitude at a selected region, then the rotation rate of the motor may be adapted as a function of the result of that comparison;

a relative difference between the displacement amplitude, represented by the last second measurements, and the desired bending displacement amplitude may be determined, then this difference may be compared with the limits of a "regulation" tolerance interval, to adapt the rotation rate of the motor when said difference is outside said regulation interval;

each rotation imposed by the motor may be detected, for example to adapt the rotation rate of the motor each time the number of signals received is equal to a selected number;

during a loading test, the motor may be ordered to drive the eccentric mass in rotation using a selected sequence of rotation rates in order to subject the sample to a selected sequence of vibratory excitations;

leaks at the sample periphery in the test zone may be detected;

two plug members may be attached to the sample at a distance from the two ends of the packer to define two zones of action in which the second selected internal pressure is applied to the sample;

at least one temperature sensor may be used at a selected region of the sample to obtain third measurements representative of the temperature of the sample at said selected region;

at least one pressure sensor may be used at a selected region of the sample to obtain fourth measurements representative of the internal pressure of the sample at said selected region;

first stress results derived from at least some of the first measurements may be compared with second radial displacement results derived from at least some second measurements to authorize the test to continue when the first results are compatible with the second results.

Other characteristics and advantages of the invention will become apparent from an examination of the following detailed description made with reference to the accompanying drawings in which.

The accompanying drawings serve not only to illustrate the invention but also to contribute to its definition, if appropriate.

Figure 1:
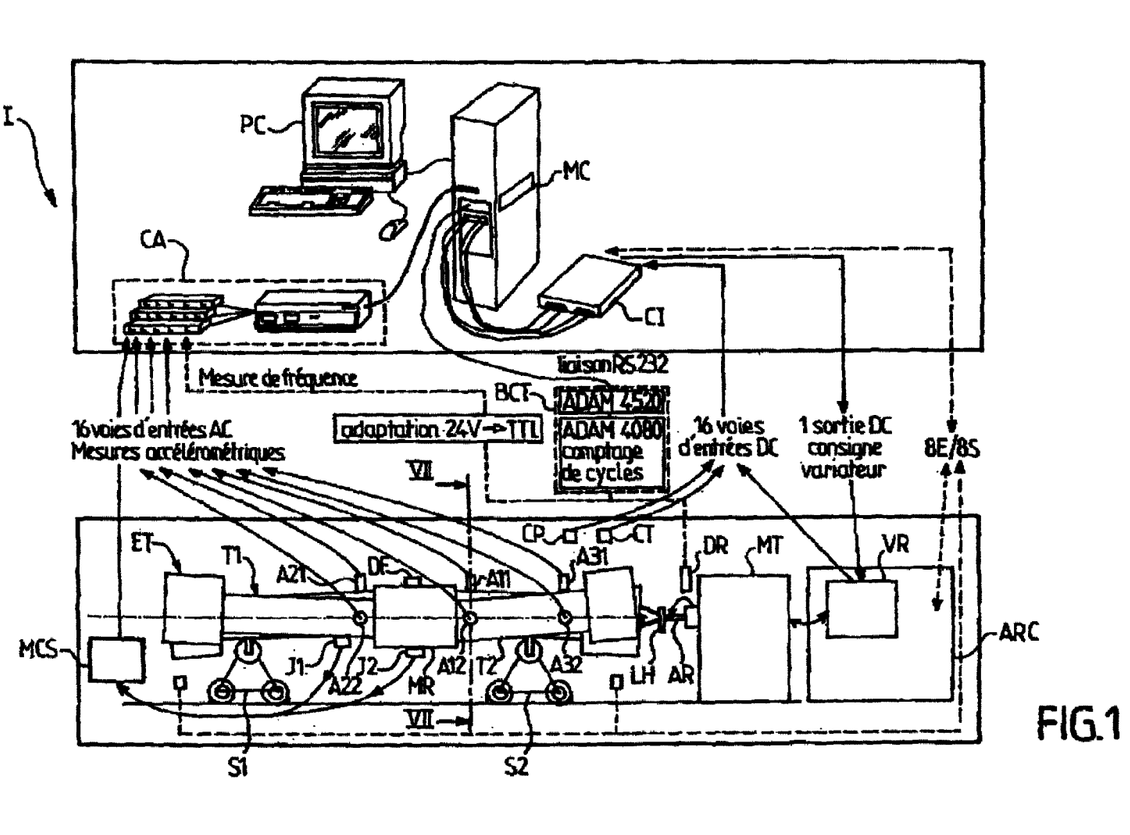
FIG. 1 is a diagrammatic illustration of an embodiment of a dynamic type mechanical loading unit in accordance with the invention.
Figure 2:
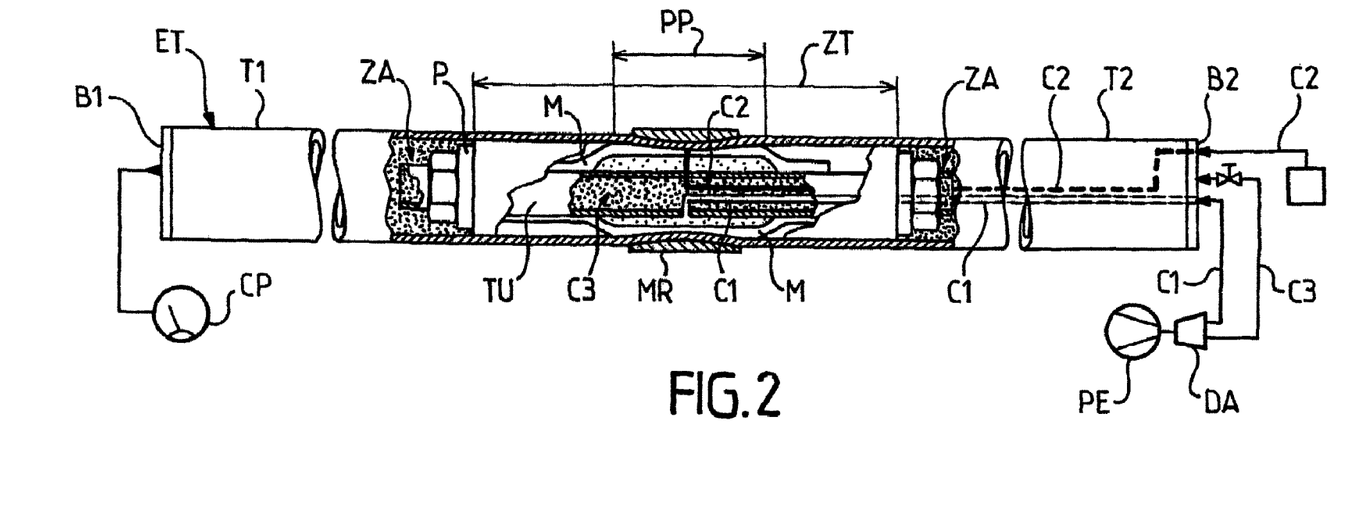
FIG. 2 is a diagrammatic illustration of an embodiment of a packer for a loading unit of the invention.

We shall initially refer to FIGS. 1 and 2 to describe an embodiment of a unit I for mechanically loading a tubular sample ET.

As indicated in the introduction, the term "tubular sample" as used here means any tube or assembly of tubes which are connected together, optionally via a coupling. As a result, the invention is adapted to the mechanical loading of tubular samples in the following forms:

a single tube (or tubular component);

two tubes (or tubular components) connected by any means, for example by welding;

a first tube (or tubular component) provided with a male threading and a second tube (or tubular component) provided with a female threading intended to cooperate with the male threading to constitute a threaded connection; and a first tube (or tubular connection) provided with a male threading, a second tube (or tubular component) also provided with a male threading, and a coupling (or tubular component) provided with two female threadings intended to cooperate respectively with the male threadings to constitute a threaded connection.

In the example shown in FIG. 1, unit I is more particularly adapted to dynamic type mechanical loads. However, the invention is not limited to this case. It concerns both dynamic type and static type mechanical loads.

The term "static type mechanical load" as used here means a load which is substantially constant over a time interval resulting from application of pressure and/or tension to a tubular sample, while the term "dynamic type mechanical load" means all other types of load which vary with time, such as that resulting from the application to a tubular sample of not only pressure and/or tension, but also a selected vibratory excitation intended to deform it by cyclic bending.

Further, the term "amplitude of a cyclic load" as used here means half of the crest-to-crest distance.

As shown in FIG. 1, a unit I of the invention comprises firstly a first portion (or bench) intended to mechanically load a sample ET. This first portion comprises (at least) a packer P (illustrated in FIG. 2) housed inside the sample ET at a test zone ZT.

In the non limiting example shown in FIG. 1, the tubular sample ET (hereinafter termed sample) is constituted by first T1 and second T2 tubes each provided with a male threading (not shown), and a coupling MR provided with two female threadings respectively cooperating with the male threadings to constitute a threaded connection which is to be tested. For this reason, the test zone ZT is located at the coupling MR. Clearly, any other zone of the sample ET may form the subject matter of a test.

The packer P, in accordance with the invention, must have a longitudinal extension (along the longitudinal axis of the tube) which is greater than that of the test zone ZT, and comprises first and second and/or third pressure means.

The first pressure means are instructed to vary locally the diameter of at least a first portion PP of the packer P to apply it against the internal surface of the sample ET at the test zone ZT.

As an example, and as shown in FIG. 2, the local variation in the diameter of the packer P may be made using a deformable annular membrane M, mounted in a sealed manner on the external surface of a tube TU of the packer P, and a selected fluid delivered at a selected pressure, between the external surface of the tube and the membrane M, via a first supply circuit C1 which forms part of first pressure means.

Membrane M is in this case located in a central region of the packer P.

Figure 3:
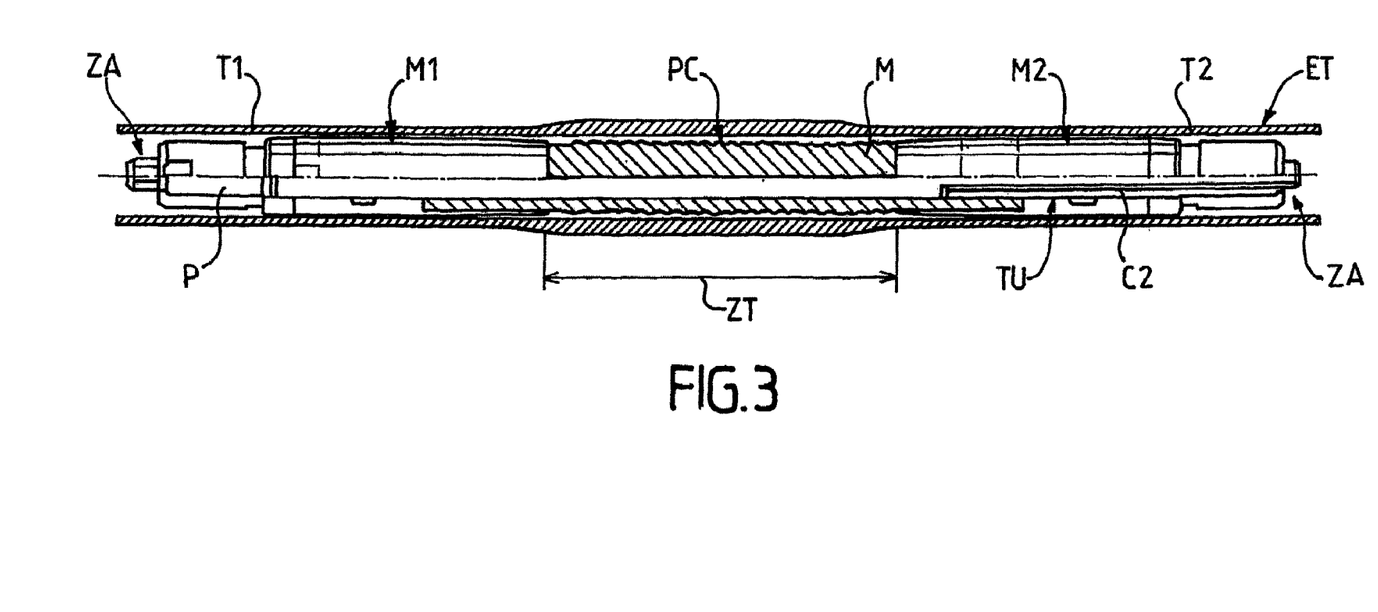
FIG. 3 is a diagrammatic illustration of a variation of a packer for a loading unit of the invention.

In a variation shown in FIG. 3, the packer P may comprise a deformable membrane M comprising a central portion PC, optionally provided with bosses or bristles allowing good fluid distribution and application of the internal pressure, and prolonged on each side by two portions M1 and M2, which are preferably smooth.

The pressurized fluid which is injected via the first supply circuit C1 allows at least a portion of the membrane M (at least M1 and M2) to be flattened against the internal wall of the sample ET and thus to immobilize the packer P inside said sample ET, at the test zone ZT, while isolating at least a portion of said test zone ZT (in particular at the central portion of the membrane).

This fluid is preferably a pressurized liquid, such as water. Its maximum pressure depends on the diameter of the sample ET. As an example, a maximum pressure of 600 bars may be envisaged for diameters of more than 7", this value of course depending on the type of pump used.

The second pressure means are instructed to exert a first selected internal pressure PI1 over a portion of the internal surface of the sample ET located facing a second portion of the packer P. In the example shown in FIG. 2, the second portion of the packer P is located at the membrane M. It constitutes a sub-portion of the first portion PP over which the membrane M extends. In contrast, in the example shown in FIG. 3, the second portion of the packer P is the central portion PC located between the two end portions M1 and M2 of the membranes M.

As an example, and as shown in FIG. 2, the second pressure means comprise a second circuit for supply of fluid C2 provided with an output which opens facing the internal surface of the sample ET. The second supply circuit C2 supplies fluid at a selected pressure to the sample zone ET located at the second portion of the packer P, allowing a first internal pressure PI1 to be applied and thus to locally place the sample ET (and more precisely here its threaded connection) under an essentially radial pressure similar to that encountered during difficult exploitation conditions.

The fluid circulating in the second supply circuit C2 is preferably a pressurized gas, such as helium. Its maximum pressure depends on the diameter of the sample ET. As an example, a maximum pressure of 600 bars may be envisaged for diameters of more than 7", this value clearly depending on the type of pump used.

The third pressure means cooperate with at least one plug member B1, which is installed at a selected distance from one end of the packer P to define in the sample ET a zone of action ZA in which the sample ET undergoes a second selected internal pressure PI2. Hence, tension may be induced in the zone of action ZA of the sample ET.

As an example, the plug member B1 is attached to one of the two ends of the sample ET. When this end is provided with a threading, attachment may be made by screwing up.

When an axial tensional loading is to be induced over the whole length of the sample ET, two plug members B1 and B2 are provided. As an example, each plug member B1, B2 is attached to one of the two ends of the sample ET. The zone of action ZA then extends between the two plug members B1 and B2. When the two ends of the sample ET are provided with a threading, the plug members B1 and B2 may be joined together by screwing up. In a variation, it may be any other means, for example a continuous weld between the end of the sample and the plug member.

The value T of the axial tensional load is, for example, given by the formula:

$$T = \pi \cdot (PI2) \cdot (ID_t^2 - ID_P^2)/4$$

in which $ID_t$ is the internal diameter of the sample ET and thus of tubes T1, T2, $ID_P$ is the internal diameter of the tube TU of the packer P, and {PI2} is the second internal pressure.

In a variation, it is possible to envisage creating two independent zones of action in sample ET, on both sides of the packer P, to exert an axial tension on each of the two portions of the sample to which they correspond.

As an example, and as shown in FIG. 2, the third pressure means comprise a third fluid supply circuit C3 charged with supplying each zone of action ZA with pressurized fluid.

To supply each zone of action ZA, tube TU of the packer P may, for example, be used. More precisely, when the tube TU is empty, it may act to channel the fluid delivered via the third circuit C3 and constitute a portion of this latter. As an example, and as shown in FIG. 2, the third circuit C3 comprises an output connected with a through orifice formed in the wall of the tube TU, allowing it to be supplied with pressurized fluid.

The fluid moving in the third supply circuit C3 is preferably a pressurized liquid such as water, for example. As an example, a maximum pressure of 600 bars may be envisaged regardless of the diameter of the sample ET.

To optimize isolation of the test zone ZT and the zone of action ZA, the pressure of the fluid moving in the first pressure means and intended to inflate the membrane M of the packer P is selected so as to be higher than the first and second internal pressures PI1, PI2.

When the same fluid moves in the first C1 and third C3 fluid supply circuits, these latter may, for example, be connected to a routing device DA which is also connected to a high pressure pump PE. Using such a routing device DA, it is possible, for example, to start by applying the selected pressure to each zone located between the tube TU and the membrane M (or its central portion PC), to immobilize the packer P inside the sample ET, and if a tension is to be exerted on the sample ET, the first circuit C1 is closed and the third circuit C3 is opened to apply the second internal pressure PI2 in each zone of action ZA.

Clearly, each supply circuit C1 to C3 may be supplied with its own high pressure pump.

In the presence of a hollow (or empty) tube TU, it is advantageous if at least a portion of the first C1 and second C2 circuits are housed inside tube TU. In this case, each output from the first circuit C1 is connected to at least one through orifice formed in the wall of the tube TU at the corresponding membrane M. In the first embodiment of packer P (shown in FIG. 2), the second circuit C2 traverses the wall of the tube TU at an orifice and is sealingly connected to another through orifice formed in the membrane M. In the second embodiment of packer P (shown in FIG. 3), the second circuit C2 is connected in a sealed manner to a through orifice formed in the wall of tube TU at the central portion PC.

To fix the stresses imposed at sample ET, but also to determine the strains and/or displacements caused by the imposed stresses, at least one strain gauge Jk is placed on the external surface of the sample ET (the index k in this case represents the number of gauges used) and/or at least one pair of accelerometers Ai1 and Ai2 (the index i in this case represents the number of pairs used).

Each strain gauge Jk is placed (for example by bonding) at a selected region of the external surface of the sample ET to deliver first stress measurements which are representative of the stress state locally undergone by this sample (at the selected region).

Preferably, at least two strain gauges are used. This number is not limiting. The higher it is, the more precisely the mapping of the stresses undergone by the sample ET and thus the more precise the mapping of the local strains.

The strain gauges Jk may be of any type. In particular, they may be uni-axial strain gauges and/or multi-axial strain gauges, for example arranged in the form of three-directional rosettes, as shown in FIG. 4.

Thanks to these strain gauges Jk, it is possible, particularly initially (preliminary reference step), to determine the stress state (uni- or multi-axial) undergone by the sample ET at one or more regions (or sections) and thus to determine the effect of a load exerted thereon.

Figures 4, 5, 6:
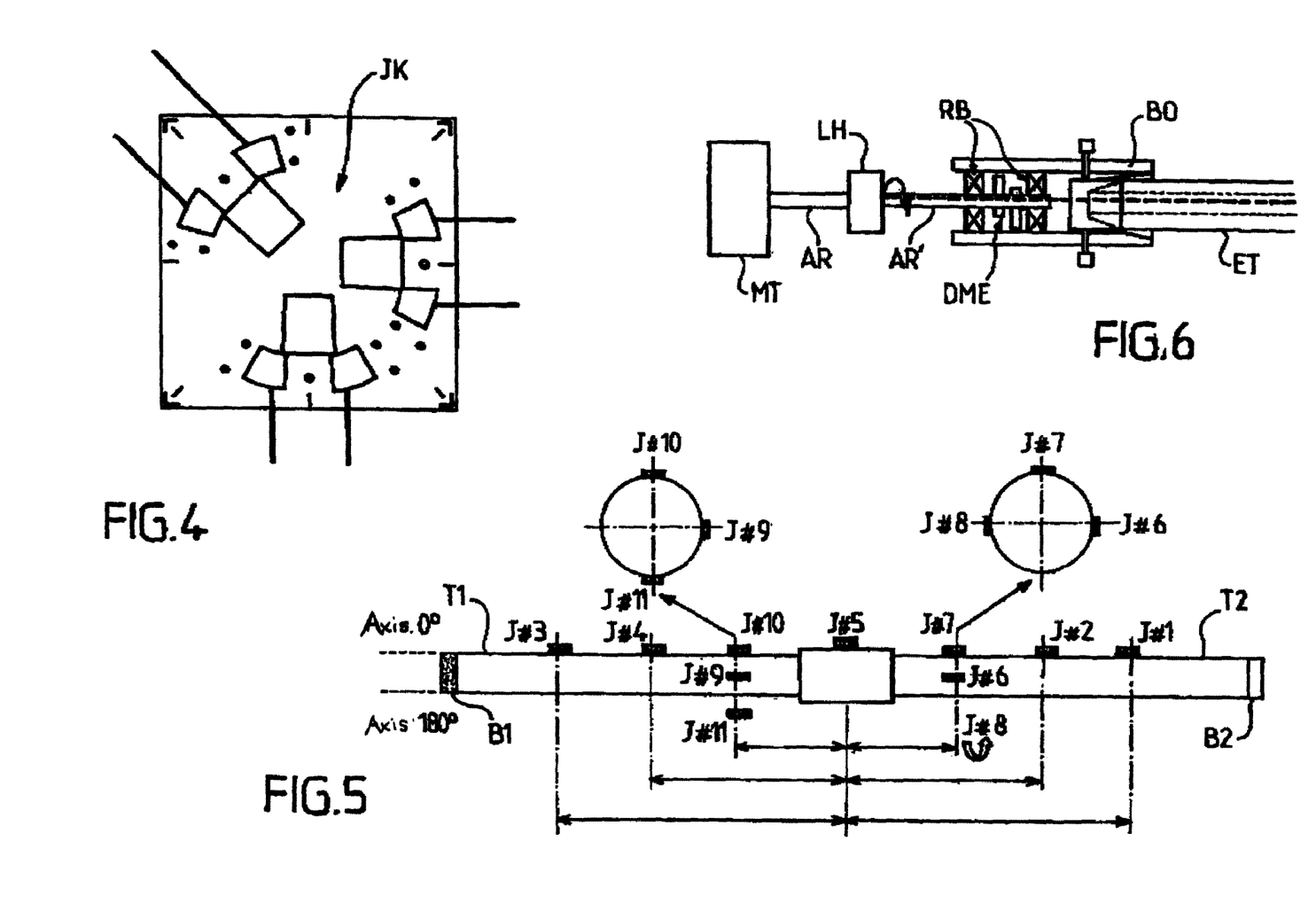
FIG. 4 illustrates an example of a strain gauge adapted to detect multi-axial stresses.
FIG. 5 is a diagrammatic illustration of one example of positioning strain gauges on a sample.
FIG. 6 is a diagrammatic illustration, in a cross sectional view, of an example of an excitation device between a motor shaft and a tubular sample.

A scheme representing an example of positioning strain gauges Jk on a sample ET, comprising two tubes T1 and T2 with an external diameter close to 240 mm and a length of 2300 mm connected by threads using a threaded coupling MR with a length of substantially 400 mm, is illustrated in FIG. 5. In this example, 11 strain gauges J1 to J11 are used:

a gauge J5 is placed substantially in the medial plane of the sample ET, i.e. in the medial place of the coupling MR, along the 0° line of the axis;
a gauge J1 or J3 is placed close to each end of the sample ET (here on tubes T1, T2 at a distance from the medial plane of about 1300 mm), along the 0° line of the axis;
gauges J2 and J4 are placed respectively in first and second intermediate sections of the sample ET (here on tubes T1, T2 at a distance from the medial plane of substantially 900 mm), along the 0° line of the axis;
triplets of gauges (J6 to J8) and (J9 to J11) are respectively placed in third and fourth intermediate sections of the sample ET (here on tubes T1, T2 at a distance from the coupling substantially equal to the external diameter of the tubes T1, T2, i.e. at a distance from the medial plane which is substantially equal to about 530 mm). The gauges of each triplet are in this case positioned at 90° to each other in two different configurations, as an example. It is also possible to use pairs or quadruplets of gauges.

Of course, a more limited number of strain gauges Jk may be used. As an example, and as shown in FIG. 1, only two strain gauges may be used, the first being placed in the centre of the sample ET and the second being placed at a certain distance from the first. In general, the positions of the strain gauges Jk depend on the region where the packer P is installed in the sample ET.

The two accelerometers Ai1 and Ai2 of each pair are placed (for example by bonding) at 90° to each other at selected regions of the external surface of the sample ET, to deliver second measurements (or signals) representative, after double integration, of the dynamic displacement locally undergone by said sample.

As an example, a first pair A11 and A12 is used associated with two other pairs of accelerometers A21 and A22, and A31 and A32.

The two accelerometers Ai'1 and Ai'2 of each other pair (i'=2 or 3 in the example under consideration) are placed (for example by bonding) at 90° to each other at selected regions on the external surface of the sample ET, different from the regions at which the two accelerometers A11 and A12 of the first pair are installed. They are intended to deliver other second measurements (or signals) representative, after double integration, of the dynamic displacement locally undergone by the sample ET at the region at which they are installed.

In the example under consideration, the pairs of accelerometers A11-A12 and A21-A22 are respectively placed on tubes T2, T1 close to the coupling and on both sides thereof, while the pair A31-A32 is disposed on the tube T2 close to the end of the sample ET.

The assembly of strain gauges (J1 to J11) and pairs of accelerometers (A11 to A32) allow the dynamic radial displacements and stresses to be determined at any point of the sample ET.

The usefulness of pairs of accelerometers will be revisited below.

The unit I may comprise sensors other than the strain gauges Jk and the pairs of accelerometers (Ai1-Ai2).

Thus, as illustrated in FIG. 1, at least one pressure sensor CP and/or at least one temperature sensor CT and/or at least one leak detector DF may be provided.

The temperature sensor CT is installed at a selected region of the sample ET, for example close to the test zone ZT. It is instructed to deliver signals (or third measurements) representative of the temperature of the sample ET at the selected region at which it is installed. Such a sensor CT can allow auto-compensation to be carried out on the measurements delivered by the strain gauges, to smooth out local temperature variations.

The pressure sensor CP is installed at a selected region of the sample ET, for example at the test zone ZT or, as shown in FIG. 2, at a plug member B1. It is instructed to deliver signals (or fourth measurements) representative of the internal pressure (PI1 or PI2) undergone by the sample ET at the selected region at which it is installed. Said sensor CP can detect a sudden variation in the internal pressure induced by a crack.

The leak detector DF is installed at a selected region of the sample ET, for example at the test zone ZT, and more precisely at the second portion of the packer P. It is instructed to detect the presence of fluid (gas) delivered via the second circuit C2, outside the sample ET. In the event of detection of a leak, the leak detector DF generates an alarm signal sent to a control module MC. Said detector DF can detect a crack in the sample ET.

Thanks to the cited loading means (first and second and/or third pressure means), it is possible to load the sample ET in a static manner.

The sample ET may then be subjected to pure pressure using the first pressure means (first circuit C1) to flatten the membrane M against the internal surface of said sample ET, and the second pressure means (second circuit C2) to locally apply a first internal pressure (radial) PI1 on the internal wall of the sample ET.

It should be recalled that under certain conditions a sample ET may undergo internal pressures which can reach 600 bars.

It is also possible to subject the sample ET to pure tension using first pressure means (first circuit C1) to flatten the membrane M against the internal surface of said sample ET, and the third pressure means (third circuit C3) to apply in each zone of action ZA a second internal pressure (axial) PI2 between the plug members B1 and B2, via the tube TU of the packer P.

Finally, the sample ET may be subjected to a combined pressure and tension using the first pressure means (first circuit C1) to flatten the membrane M against the internal surface of said sample ET, second pressure means (second circuit C2) to locally apply a first internal pressure (radial) PI1 to the internal wall of the sample ET, and the third pressure means (third circuit C3) to apply in each zone of action ZA a second internal pressure (axial) PI2 between the plug members B1 and B2, via the tube TU of the packer P.

It is important to note that a mechanical loading test may comprise a single phase in which the intensity of each load (pressure and/or tension) is substantially constant, or a sequence of at least two phases in which at least one of the load intensities varies from one phase to the other.

A test may in particular be carried out in several phases, each carried out with a particular combination of loads in order, for example, to explore a portion of the contour of the Von Mises ellipse or any other line defined from the ellipse, for example a portion of the homothetic line of the ellipse.

A test is defined by a file parameterized by a technician. It may optionally be resumed if it has been interrupted. Said file contains all of the information relating to the sample ET (reference, diameter) and to the pressures in circuits C1 to C3, also the measurements and monitoring parameters.

As shown in FIG. 1, when it is desired to load the sample ET in a dynamic manner, the portion of the unit I dedicated to loading must comprise means, complementary to the pressure means (M, C1 to C3) and coupled to the sample ET in order to subject it to a selected vibratory excitation intended to deform it by cyclic bending.

Said complementary means are preferably in the form of two support means S1, S2 of the sample ET, and a rotary motor MT, connected to excitation means coupled to one end of the sample ET.

As an example, and as shown in FIG. 1, each support means S1, S2 is produced in the form of a mobile support the position of which may vary as a function of requirements as regards the load and the dimensions of the sample ET. As an example, each mobile support S1, S2 is constituted by a flexible jack of the type sold under the trade name "Pneuride" by Firestone-Bridgestone.

As shown in FIG. 6, the excitation means are, for example, constituted by a casing BO firmly attached to one end of the sample ET and rotatably housing an eccentric mass device DME rotatably mounted on a support shaft AR'. This eccentric mass device DME defines an unbalanced mass for the end of the sample ET under consideration.

The connection between the motor MT and the support shaft for the excitation means may be a direct connection or a homokinetic connection LH, for example of the universal joint or plastic joint type, which ensures coupling between an output shaft AR of the motor MT and the excitation means.

A coupling by homokinetic connection as shown in FIG. 1 has the advantage of allowing the motor MT to be fixed to the frame of the unit and of not subjecting the motor to strong vibrations.

Direct coupling necessitates attaching the motor to the end of the sample ET but has other advantages which will be discussed below.

As an example, it is possible to use a motor MT with a power of 15 kW which can drive a shaft AR at a maximum rotation rate of about 3000 rpm.

As an example, and as shown in FIG. 6, the device with an eccentric mass DME is rotatably mounted in the casing BO by means of two ball bearings RB.

When the motor MT drives the eccentric mass in rotation, this constrains the casing BO to vibrate radially. Since the sample ET is placed on two supports S1 and S2 and one of its ends is fixed to a casing BO, the sample ET is thus also constrained to vibrate. It is thus subjected to a selected vibratory excitation which is (mainly) a function of the unbalanced mass defined by the eccentric mass DME and which causes its deformation by bending. More precisely, a bending wave, the fundamental frequency of which is equal to that of the rotation of the unbalanced mass, propagates in the sample ET in a rotary manner with respect to its longitudinal axis at rest.

This type of excitation can reproduce a load with a rotating stress and/or a rotating strain, for example of the type generated by the displacements of an offshore platform and/or marine currents and/or by rotation of a tubular string which is dropped into a well which deviates from the vertical.

Highly preferably for the stability of the sample during the test, two supports S1 and S2 are provided at vibratory nodes.

This is generally not possible in the case of the unit with a homokinetic connection LH as this is necessarily located at a vibratory node. Only the support S1 may then be disposed at a vibratory node. The other support S2 may for this reason be subjected to large vibrations.

In the case of a direct connection between the motor MT and excitation means, two supports S1, S2 may be located at the vibratory nodes, which is advantageous and preferred.

Figure 7:
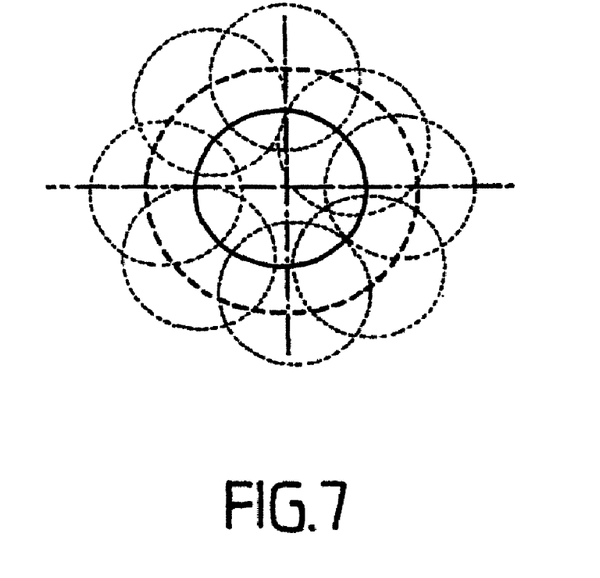
FIG. 7 is a diagrammatic illustration of the displacement of a sample in the case of a dynamic type mechanical load.

The trajectory followed by the sample ET, at the section indicated by arrows VII-VII in FIG. 1, is diagrammatically shown in FIG. 7. The central circle, as a continuous line, shows the initial position of the sample ET at rest; the dotted circles indicate successive positions of the sample ET when it is subjected to a vibratory excitation, and the circle in dashed lines indicates the trajectory of the longitudinal axis of the sample ET when it is subjected to the vibratory excitation.

A stress amplitude and/or radial bending displacement which is substantially uniform may thus be imposed over the whole circumference of the sample ET.

As an example, an eccentric mass is used with a mass of 30 kg or less and a "resolution" vibratory excitation mode 1 the resonance frequency of which is in the interval from about 20 Hz to about 30 Hz. It may thus cause cyclic bending the amplitude of the radial displacement of which may exceed a hundred millimeters, for example about 120 mm at the centre of the sample ET (in this case occupied by the threaded connection with the coupling MR), when its diameter is 16" and it is several metres long.

It is important to note that the closer the rotation frequency of the motor is to the resonance frequency, the greater the amplitude of the bending waved to which the sample ET is subjected. The rate of rotation of the motor MT may be selected by means of a variator VR receiving instructions (reference variable) from a control module MC which will be discussed below.

An interval of rotation rates is selected which is below the resonance frequency of the sample ET in mode 1. This resonance frequency depends on the parameters of the sample ET (such as the length of the material) and on other parameters (such as the type of packer P and the fluids contained in the sample ET). It may theoretically be determined from theoretical computations but, because of the complexity of the parameters, it is more likely to be determined from tests with and without an unbalanced mass (DME). In general, the shorter the sample, the higher its resonance frequency.

The excitation force F to be applied to the end of the sample ET, to obtain a given displacement amplitude of the sample depends on the length of the sample. The shorter the sample ET, the closer the excitation force has to be to the displacement amplitude (or stress) in the given sample.

The excitation force as a function of the unbalanced mass to be used (with mass M), the radius r from the centre of inertia of the unbalanced mass and the rotation rate N of the motor is given by the formula:

$$F = M \cdot r \cdot \omega^2 \cdot \sin \omega t$$

In which $\omega = 2\pi \cdot N$ and N is given in revolutions per second.

Typically, a rotation rate N is selected which is smaller than the resonance frequency of mode I by several hertz.

In order to control the rotation rate of the motor MT, the unit I comprises a control module MC which is, for example, installed in a computer PC. More precisely, the control module MC is instructed to regulate the rotation rate at which the motor MT must drive the eccentric mass DME so that the sample ET is subjected to a vibratory excitation to cause a substantially constant strain by cyclic bending of the stress amplitude or radial displacement, determined during a preliminary phase.

Providing the strain by initial bending is preferably carried out during a preliminary reference step over a given time interval. It is theoretically possible to determine the desired rotation rate of the motor MT which will induce a desired bending strain of the sample ET, depending on the unbalanced mass used. However, in practice, rate adjustments must generally be carried out so that the real strain corresponds to the desired strain.

The preliminary reference step thus consists of imposing on the motor MT, for example using a control module MC, the initial relatively low rate, then for example reading the amplitude of the stress undergone by the sample ET using at least one of the strain gauges Jk. By comparing the amplitude of the measured stress to that desired, it may be determined whether the rotation rate is suitable (in the case of equivalence) or whether the initial rate must be adapted (in the case of difference). The comparison may be made manually by the operating technician or automatically by the control module MC.

If the real strain is not equivalent to the desired strain, the rotation rate is increased by a given increment so that the new rotation rate induces the desired stress amplitude. Again, this incrementation of the rotation rate may be made manually by the operating technician or automatically by the control module MC.

The various (first) stress measurements carried out to determine the rotation rate to be applied are termed the first reference measurements.

Instead of (first) stress measurements, it is possible to use (second) acceleration measurements, delivered by the first pair of accelerometers Ai1 and Ai2, as well as possibly by the other pairs of accelerometers Ai'1 and Ai'2, which then serve as reference measurements for the radial displacements undergone by the sample ET, and to define second reference measurements when the rotation rate inducing a given displacement amplitude of the sample is determined.

It is important to note that the accelerometers used for the second measurements do not have to be disposed at vibratory nodes, nor close thereto.

Once the rotation rate has been determined from first or second reference measurements, the loading test can commence. Any type of test may be envisaged.

As an example, it may be possible to deform the sample only in cyclic bending thanks to the excitation means driven by the motor MT. The invention is applicable to samples which are only tested in cyclic bending (purely dynamic conditions without superimposed cyclic loads). In this case, only the complementary means are used (the packer, the pressure means and the plug member not then being necessary).

It is also possible to deform the sample ET by cyclic bending by means of excitation means driven by the motor MT, while subjecting it to pure pressure using first pressure means (first circuit C1) to flatten the membrane M against the internal surface of said sample ET, and the second pressure means (second circuit C2) to locally apply a first internal pressure (radial) PI1 on the internal wall of the sample ET.

It is also possible to deform the sample ET by bending by means of excitation means driven by the motor MT, while subjecting it to pure tension using the first pressure means (first circuit C1) to flatten the membrane M against the internal surface of said sample ET, and the third pressure means (third circuit C3) to apply in each zone of action ZA a second internal pressure (axial) PI1 between the plug means B1 and B2, via the tube TU of the packer P.

Finally, the sample ET can be deformed by bending by means of the excitation means driven by the motor MT, while subjecting it to a pressure combined with tension using the first pressure means (first circuit C1) to flatten the membrane M against the internal surface of said sample ET, the second pressure means (second circuit C2) to locally apply a first internal pressure (radial) PI1 to the internal wall of the sample ET, and the third pressure means (third circuit C3) to apply a second internal pressure (axial) PI2 in the zone of action ZA between the plug members B1 and B2, via the tube TU of the packer P.

It is important to note that the use of the packer, pressure means and plug members fixed to the sample of the invention can highly advantageously superimpose a combination of static loads with a cyclic dynamic load, which prior art test units using jacks cannot carry out, and to select a combination of given static loads, which prior art units which offer simple internal pressurization using a fluid cannot offer.

It is also important to note that a dynamic loading test may comprise a single phase, in which the intensity of each load (deformation by bending and pressure and/or tension) is substantially constant, or a sequence of at least two phases in which the intensity of at least one of the loads varies from one phase to another. As an example, a dynamic loading test may comprise a sequence of phases in which the pressure and/or tension are maintained substantially constant while the rotation rate of the eccentric mass (DME) varies from one phase to another (for example in an increasing manner).

As indicated above, a test is defined by a file parameterized by a technician. Said file contains all of the information relating to the sample (reference, diameter), to the load condition (mass of unbalanced mass, rate of rotation (frequency) of each phase of a sequence, number of cycles (or revolutions for each phase) and the pressures of circuits C1 to C3, as well as the measurement and monitoring parameters.

It should be recalled that the fatigue phenomenon is characterized by the appearance of a crack which is propagated through the wall of the sample, following a certain number of cycles (or revolutions of the motor).

When a fatigue crack propagates in the sample, there is a loss of "monolithism" of the sample and the amplitude of the stress and/or radial displacement that the sample undergoes varies if the rotation rate (or frequency) remains constant.

Other events before the appearance of a fatigue crack may cause variations in the amplitude of the stress or displacement.

As a result, if the deformation of the sample ET in stress or in displacement has to remain substantially constant from the start to the end of a loading test, the unit I must include an error correction system relying on regulation of the rotation rate, imposed on the unbalanced mass (DME) by the motor MT, as a function of a comparison between the measures carried out and the reference measurements.

Regulation of the rotation rate resides in at least:
the first reference measurements (stress) representative of the amplitude of the stress initially undergone by the sample ET;
the first subsequent measurements representative of the amplitude of the stress undergone by the sample ET during the test.

In a variation, the regulation of the rotation rate resides in at least:
the second reference measurements representative of the displacement amplitude or amplitudes at each section of the sample ET provided with a pair of accelerometers and corresponding to the initial strain amplitude;
the subsequent second measurements representative of the displacement undergone by the sample ET during the test at its section provided with the first pair of accelerometers A11 and A12;
and optionally the other second measurements representative of other displacements undergone by the sample ET at its other sections provided with another pair of accelerometers Ai'1 and Ai'2. The control module MC may, for example, determine a relative difference between the displacement amplitude, provided by last second measurements, and the desired bending displacement amplitude, then compare this difference with the limits of a selected "regulation" tolerance interval, to adapt the rotation rate of the motor MT each time the difference is outside the regulation interval. Exceeding the threshold is considered here as an error which must be corrected.

The relative difference is, for example, compared with the limits of a regulation interval fixed by a percentage, for example ±2.5%. If the relative difference between the correct value and the last value is outside the interval in the interval −2.5% to +2.5%, then the error must be corrected.

A second "monitoring" tolerance interval, for example double the regulation interval and centred thereon, may be defined to trigger a stop to the test if the relative difference is located outside this second interval.

The foregoing statements regarding displacements can be transposed to stresses.

Correction of the rotation rate made by the control module MC is based on measurements made at a selected frequency. As an example, this frequency corresponds to the rotation frequency of the shaft AR driven by the motor MT. Each rotation of the shaft AR is, for example, detected by a rotation detector DR and results in the generation of a signal intended for the control module MC. Hence, each time the control module MC has received a number of signals equal to a selected number, it interrogates the accelerometers and/or gauges concerned by the control system and uses their (first and/or second) measurements to implement said control. The rotation detector DR is, for example, of the optical type (it comprises, for example, a reading laser, possibly of the type sold by Keyence).

It is important to note that the control system may be effected from measurements delivered by at least some of the gauges or from measurements delivered by at least some of the accelerometers (displacements) or from measurements delivered by at least some of the accelerometers (displacements) at the same time as measurements delivered by at least some of the gauges (stresses).

One example of a control system computation residing in (second) measurements from accelerometers is described hereinafter (the computation may be carried out in the same manner on the (first) stress measurements).

This computation example starts from the hypothesis that the operational strain of the sample ET is of first order, and as a result that the amplitude of the displacement at the excitation frequency at each section provided with a pair of accelerometers is directly linked to the stress undergone by the sample ET. Under these conditions, to keep the initial stress constant, corresponding to the initial strain, it is sufficient to maintain each displacement amplitude constant.

Each time the control module MC receives a signal (or top tour) from the rotation detector DR, it recovers the (second) measurements made by each pair of accelerometers and deduces a first maximum amplitude value and the corresponding phase value around the excitation frequency.

Each maximum amplitude value is, for example, corrected from a spectral analysis of the time signal delivered by the accelerometers, as a function of the frequency resolution and the values for the peaks at frequency fn and at frequencies $f_{n-1}$ and $f_{n+1}$ on both sides of $f_n$ using an algorithm such as that presented below.

If $a_n$ is the maximum amplitude at frequency $f_n$ and $a_{n-1}$ and $a_{n+1}$ are the amplitudes at frequencies $f_{n-1}$ and $f_{n+1}$, and ρf is the frequency resolution, then the corrected amplitude (of acceleration) $a'_n$ at frequency $f_n$ is given by the relationship $a'_n = a_n/\rho a$, where:

$$\Delta' f = \frac{\Delta f}{1 + \max\left(2, \frac{a_n}{\min(a_{n-1}, a_{n+1})}\right)}$$

and $$\Delta a = \frac{\sin\left(\frac{\pi \Delta' f}{\Delta f}\right)}{\frac{\pi \Delta' F}{\delta F}}$$

These corrected amplitudes (of acceleration) are then converted into displacements (u) by a double spectral integration, where:

$$u = \frac{a'_n}{(2\pi f)^2}$$

The two signals delivered by a pair of accelerometers representative of a theoretical displacement are in this case sinusoidal in form.

The orbit of these two signals on the same section of the sample ET describes an ellipse the major axis of which constitutes the maximum amplitude of the displacement on the section of the sample ET.

Figure 8:
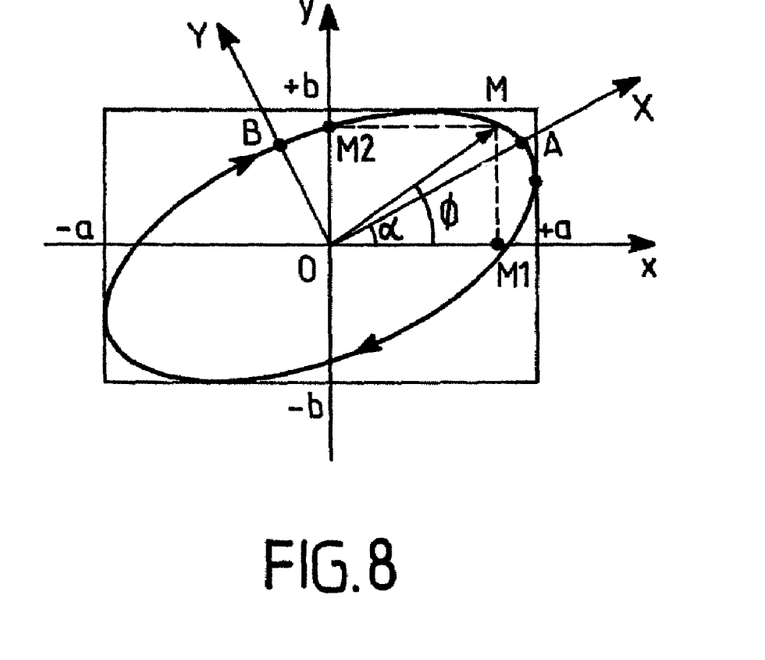
FIG. 8 is a diagram illustrating part of the dynamic displacement computation using an ellipse.

As shown in FIG. 8, this ellipse is inscribed in a rectangle the sides a and b of which correspond to the measured and corrected amplitudes (of acceleration). Its principal axes are offset by an angle $\alpha$ to the x, y axes along which the accelerometer pairs take their measurements.

The parametric equations for the two signals may be expressed in the following manner (shown in FIG. 8 for a point M, given, for example, by the top tour):

$$OM_1: x = a \cos \omega t$$

$$OM_2: y = b \cos(\omega t + \Phi), \text{ where } \Phi \in [0, 2\pi]$$

Where $\Phi$ is a dynamic dephasing between the signals from the two accelerometers.

On investigating an equation of an ellipse of the form:

$$\frac{X^2}{A^2} + \frac{Y^2}{B^2} = 1$$

and by carrying out a change of index by rotation by an angle $\alpha$, the following formula is obtained:

$$\alpha = 1/2 \arctan\left(\frac{2\cos\Phi ab}{a^2 - b^2}\right)$$

where $\alpha \in [0, \pi/2]$

The principal axes of the ellipse are then deduced in the following manner:

$$A = \sqrt{\frac{a^2 b^2 \sin^2 \Phi}{b^2 \cos^2 \alpha + a^2 \sin^2 \alpha - 2ab \sin\alpha \cos\alpha \cos\Phi}}$$

$$B = \sqrt{\frac{a^2 b^2 \sin^2 \Phi}{b^2 \sin^2 \alpha + a^2 \sin^2 \alpha - 2ab \sin\alpha \cos\alpha \cos\Phi}}$$

The maximum of A and B then corresponds to the maximum amplitude achieved.

It can be verified that by putting $\Phi = 90°$ (which corresponds to an absence of dynamic dephasing and thus only to a static dephasing between the accelerometers of a pair), it can be shown that $\alpha = 0°$, A=a and B=b.

The control module MC carries out the computation for each section of the sample ET provided with a pair of accelerometers and initially selected by the technician.

The values for the amplitude of the displacement of each section may optionally be displayed on the screen of the computer PC. This display may, for example, be in the form of a superimposition of the last ellipses obtained using each pair of accelerometers of each section for analysis. The various superimposed ellipses may be scaled with respect to the largest displacement measured (with respect to the largest range of input values).

Preferably, the control module MC determines the selected relative difference between each displacement amplitude which it has determined and the amplitude of the displacement corresponding to the (second) initial reference measurements. This difference is then compared with the limits of a regulation tolerance interval which is defined by the technician prior to the start of the loading test.

When the tolerated relative distance (or tolerance percentage) is satisfied at each section of the sample ET, the loading test is continued with the same rotation rate as before, or with a new rate (or reference variable) if said test includes a new phase with a different displacement amplitude.

When the relative difference (or percentage tolerance) is not satisfied at least one of the sections of the sample ET, the control module MC applies a positive or negative increment (defined by the technician prior to the start of the loading test) depending on the value of the difference, to the current value of the rotation rate, so as to define the new value (or reference variable) for the rate of the motor MT.

When an increment has been applied, it is possible, for example, to provide that the control module MC continues its computations but does not apply a new correction (new increment) for a delay initially defined by the technician. This rule is intended to allow the unit I to stabilize its response.

It is important to note that if at a given moment the frequency, which corresponds to a new rate of rotation (or reference variable) determined by the control module MC exceeds a maximum frequency initially defined by the technician, which is slightly smaller than the resonance frequency of the sample ET, the loading test is stopped.

It is also important to note that the minimum response time for the control system corresponds to the selected frequency resolution.

When the control system acts only on (first) stress measurements, the reference variable may be corrected by adding positive or negative increments for the rotation rate. As an example, the relative stress (gauges) differences with respect to the limits of a tolerance interval on the stresses may be compared. In this case, it may be decided to increase the rate of rotation by an increment in the event if the relative stress difference goes under the lower limit of the regulation tolerance interval. Similarly, it may be decided to reduce the rate of rotation by one increment if the relative stress difference goes above the upper limit of the second regulation tolerance interval. If the relative stress difference is outside a monitoring tolerance interval twice the regulation tolerance interval and centred thereon, it may be decided to stop the motor MT and thus the test.

When the control system acts only on (second) accelerometric measurements, the reference variable may be corrected in a similar manner by adding positive or negative increments of the rotation rate: an increase in the rotation rate by one increment if the relative displacement difference falls short of the lower limit of the tolerance interval and a reduction in the rotation rate by one increment if the relative displacement goes above the upper limit of the second tolerance limit. If the relative displacement difference is outside a monitoring tolerance interval twice the regulation tolerance interval and centred thereon, it may be decided to stop the motor MT and thus the test.

When the control system acts both on (second) accelerometric measurements and on (first) stress measurements (gauges), the reference variable may also be corrected by adding positive or negative increments. As an example, the relative displacement differences (accelerometers) may be compared with a tolerance interval on the displacements (as a percentage), as indicated above, and the stress differences (gauges) may be compared with respect to a tolerance interval on the stresses (as a percentage). In this case, it may be decided to increase the rate of rotation by one increment if the relative stress difference falls short of the lower limit of the second tolerance interval regardless of the value of the relative displacement difference provided it is within the monitoring tolerance interval associated therewith. Similarly, it may be decided to reduce the rotation rate by one increment if the relative stress difference goes above the upper limit of the second tolerance interval, regardless of the value of the relative displacement difference provided that it is within the monitoring tolerance interval associated therewith. When the relative stress difference or displacement difference is outside the monitoring tolerance interval associated therewith, it may be decided to stop the motor MT and thus the test. It may also be decided that if the relative stress differences and displacement differences require increments in rotation rates of an opposite sign, the test is stopped.

The unit may also function in a "degraded" regime. In this regime, essentially used in the presence of a large fatigue crack because the fatigue crack can only limit the effect of the stress undergone by the sample ET, the rotation rate is increased by one increment when departing from the regulation tolerance interval.

We shall now describe in detail, with reference to FIG. 1, the equipment allowing the unit I to implement its regulation, or more simply to take the measurements made by its various sensors, and in particular its strain gauges Jk and its pairs of accelerometers Ai1, Ai2.

The computer PC is, for example, equipped with an analogue and digital input/output card CI and an analysis card CA.

The analogue and digital input/output card CI is, for example, of the Measurement Computing PCI/DAS1602/16 type. Said card comprises, for example:

- 8 digital inputs enabling to obtain logic information on and for the loading means (or bench), such as an authorization to start or detection of the presence of the sample ET. These 8 inputs are preferably parameterizable by the technician;
- 8 analogue inputs enabling to receive "slow" signals (or measurements) which are continuous (or DC), such as pressures (CP) or temperature (CT);
- 4 digital outputs enabling to provide instructions regarding the function of the control box ARC which comprises the variator VR. One of the digital outputs is, for example, used as a watchdog. The control module MC is thus instructed to change the state of this watchdog output at regular intervals. This change of state is supplied to a time lag relay of the control box ARC. Hence, in case of accidental stoppage of the application (caused, for example, by a logic breakdown or a component breakdown), the time lag relay stops the function of the motor MT;
- 1 analogue output can impose the reference variable of the variator VR.

The analysis card CA is, for example, of the type OROS OR25 PC_PACK II-316 type (16 inputs). It is instructed to collect and analyze the alternating measurements (AC) delivered by certain sensors (strain gauges, accelerometers), in the form of dynamic signals.

The measurements from the strain gauges Jk are preferably conditioned by a signal conditioning module MCS, for example of the HBM measurement technology type, before being transmitted to the analysis card CA.

The analysis card CA is, for example, connected to the computer PC via a PCI/PCMCIA interface.

The portion dedicated to analysis of signals within the analysis card CA comprises, for example, an OR25 analyzer comprising a type OR763 analysis module for frequency analysis by fast Fourier transform FFT, and a type OR773 recorder module.

The measurement mode used by the OR25 analyzer is, for example, real time FFT. Because of the range of vibratory excitation frequencies (typically 10 to 50 Hz), the analysis band to be used must be defined between about 50 and 100 Hz.

When the rate adjustment variation step with the potentiometer of the variator VR is of the order of $2/100^{th}$ of a revolution, this corresponds to a variation in frequency of the order of 0.1 Hz. The resolution in the measurement (which is defined by the ratio between the analysis band and the number of spectral lines) must thus be less than or equal to this variation step. The duration of each measurement is inversely proportional to this frequency resolution: as an example, for a resolution of 0.05 Hz, the measurement duration is 20 seconds. This resolution is adjusted in the analyzer using the number of spectral lines. The technician has the possibility of modifying this resolution adjustment so as to control the duration of the measurement.

The OR25 analyzer carries out module and phase spectral measurements, synchronized on the tachometric signal delivered by the rotation (or revolution or cycle) detector DR to which it is coupled. These measurements are preferably time averaged. An adjustment of the number of timing means may be envisaged The control module MC computes and enables to display the duration of an acquisition on the computer PC screen. By definition, the duration of the time interval between two control system measurements is equal to the product of the acquisition period and the defined number of means.

It is advantageous to manage saturation of the input channels of the analysis card CA. In this case, for each channel of the analyzer, a interval of input values is specified for the analogue/digital converter of the analysis card CA. The analyzer can detect saturation of the converter during the measurement, characteristic of an erroneous measurement. Adjustment of the interval of input values covers the whole digital dynamic range of the converter (for example 16 bits) for the measurements.

The OR25 analyzer may also have a self-calibration mode for the ranges of input values. From maximum signals, it then determines optimal range adjustments for each of the input channels. A safety margin may optionally be added to each optimum.

The technician may thus specify, for each input channel, a range of fixed or automatic input values (and an optional associated safety margin). It is important to note that during the test any saturation detection during a measurement causes an event to be recorded and stoppage of the test.

The OR25 analyzer provides for each pair of accelerometers used a phase value cadenced by each tachometric signal (or top tour) delivered by the rotation detector DR. This phase value is in fact representative of the relative dephasing between the two accelerometers of a pair installed in a section of the sample ET. The OR25 analyzer offers perfect synchronization of the various signals measured with respect to each top tour signal.

The phase measurement can only be made correctly if the top tour signal is present. In the case of a loss of tachometric signal, the analyzer does not trigger the measurements. The control module MC detects a problem when no top tour signal is detected within a selected period (for example 2 seconds).

The strain gauge signals Jk are preferably collected and analyzed at the same time as the signals delivered by the pairs of accelerometers. Next, the change in the stress undergone by the test sample in each section equipped with a strain gauge Jk is monitored on the screen of the computer PC.

The output from the rotation detector DR is, for example, connected not only to the analysis card CA but also to a revolution counter box BCT, such as an ADAM 4080 box, which is itself connected via a RS485 bus to a communication box BCN, such as an ADAM 4520, connected to a series port of the computer PC via a RS232C interface.

Counting the number of revolutions allows the number of bending cycles undergone by the sample from start-up of the test until it stops (by breakage of the sample, leak of internal pressure, incapacity of control system in the specified tolerance interval, function too close to the resonance frequency, or any other event which could cause stoppage of the test) to be determined.

Counting the revolutions (or rotations or cycles) by the control module MC is made by regularly reading fields on the series port. As an example, each communication error recognized during regulation by the control system causes a count defect in the number of revolutions (or cycles) which interrupts the control system.

The control module MC may be produced in the form of electronic circuits (hardware), software modules (or informatics) or a combination of electronic circuits and software modules.

The invention is not limited to the implementations of the loading unit and the loading method described above, only by way of example, but it encompasses all variations which the skilled person may envisage in the context of the claims below.

The invention is aimed, for example, at being applied to a tubular sample constituted by two tubes connected together by any other connection means apart from threadings.

The samples may then be constituted by two tubes connected by any type of welding process, the term "welding process" as used here being taken in the broad sense and encompassing welding by fusion (with or without added material) or without fusion, braze welding or brazing, solid state and/or liquid state diffusion (described, for example, in patent documents EP-A-1 418 376, U.S. Pat. No. 6,288,373, WO-A-99/08828), or by interpenetration of the materials of the surfaces to be connected, of the magnetoforming or explosion forming type, for example.

The samples may also comprise two tubes connected via one or more connection pieces such as flanges attached to the ends of the tubes.

The connections between the tubes may also be connections of the type described in U.S. Pat. No. 5,681,059, functioning by cooperation of series of male and female annular reliefs and grooves disposed on the external surface of a tube and the internal surface of the other tube.

The invention is also applicable to a tubular sample constituted by more than two tubes connected one to the next by any connection means. A test zone may be defined at each connection. In this case, a plurality of packers may be used. Alternatively, it may be possible to use a packer on which a plurality of test zones is defined. It is also possible to use a plurality of second pressure zones to exert first internal pressures independently of each other in each of the test zones.

It is also possible to use third pressure means to exert second internal pressures which are independent of each other.

What is claimed is:

1. A unit for mechanically loading a tubular sample, comprising:
   at least one packer housed in the sample at a test zone, having a longitudinal extension greater than that of the test zone and comprising:
   i) first pressure means for locally varying the diameter of at least a first portion of the packer so as to apply the packer against an internal surface of the sample at the test zone,
   ii) second pressure means for exerting a first selected internal pressure over a portion of the internal surface, located at a second portion of said packer, and
   iii) third pressure means for cooperation with at least one plug member, attached to the sample at a distance from one end of the packer to define a zone of action, so as to exert on the sample a second selected internal pressure at the zone of action.

2. A unit according to claim 1, further comprising at least one strain gauge configured to be placed at a selected region of an external surface of the sample so as to deliver first stress measurements representative of a stress state undergone by the sample at the selected region.

3. A unit according to claim 1, further comprising at least two strain gauges configured to be placed in two different selected regions of the external surface of the sample so as to deliver first stress measurements representative of a stress state undergone by the sample at each of the selected regions.

4. A unit according to claim 1, further comprising:
   two support means to support the sample;
   a rotary motor coupled to an excitation means, including a device with an eccentric mass coupled to one end of the sample and defining an unbalanced mass; and
   control means to order rotation of the eccentric mass by the motor at an adjustable rate, so as to subject the sample to a selected vibratory excitation, which is a function of the unbalanced mass, to cyclically deform the sample by bending.

5. A unit according to claim 4, wherein at least one of the support means is configured so that its position substantially correspond to a vibration node of the sample.

6. A unit according to claim 4, wherein the control means is configured to adapt the rotary speed of the motor as a function of an amplitude of a stress to which the sample is to be subjected.

7. A unit according to claim 4, further comprising at least one pair of accelerometers configured to be placed at 90° to each other in selected regions of the external surface of the sample to deliver second measurements representative of a displacement undergone by the sample, and wherein the control means is configured to adapt rotary speed of the motor as a function of last second measurements provided by the pair of accelerometers, so that an amplitude of radial displacement by bending undergone by the sample at a selected region remains substantially constant.

8. A unit according to claim 7, comprising at least two pairs of accelerometers, the accelerometers of each pair being configured to be placed at 90° to each other at other selected regions of the external surface of the sample so as to deliver other second measurements taken at other selected regions and representative of displacements undergone by the sample at the other selected regions, and wherein the control means is configured to produce combinations of last second measurements so as to adapt a rotation rate of the motor as a function of the combinations so that an amplitude of the bending displacement undergone by the sample at the selected regions remains substantially constant.

9. A unit according to claim 8, wherein the tubular sample is constituted by at least two tubular components connected together at the test zone, and two of the pairs of accelerometers are placed on both sides of the connection.

10. A unit according to claim 7, wherein the control means is configured to compare at least the last second measurements delivered by at least one of the pairs of accelerometers with second reference measurements representative of an initial displacement amplitude corresponding to a desired bending displacement amplitude at the selected region, then to adapt a rate of rotation of the motor as a function of a result of the comparison.

11. A unit according to claim 10, wherein the control means is configured to determine a relative difference between the displacement amplitude represented by the last second measurements and the desired displacement amplitude by bending, then to compare this difference with a regulation tolerance interval, so as to adapt the rate of rotation of the motor when the difference is outside the regulation interval.

12. A unit according to claim 4, further comprising a device for detecting rotation suitable to detect each rotation imposed by the motor.

13. A unit according to claim 12, wherein the rotation detection device is configured to send to the control means a signal representative of each detected rotation, so that the control means adapts a rotation rate of the motor each time a number of signals received is equal to a selected number.

14. A unit according to claim 1, wherein the packer comprises a substantially non-deformable support on which an annular deformable membrane is mounted, and wherein the first pressure means comprises a first fluid supply circuit configured to introduce a selected fluid between the substantially non-deformable support and the membrane so as to apply a selected pressure.

15. A unit according to claim 14, wherein the fluid is a pressurized liquid.

16. A unit according to claim 1, wherein the second pressure means comprises a second fluid supply circuit comprising a fluid output opening facing the internal surface of the sample so as to apply the selected first internal pressure.

17. A unit according to claim 16, wherein second fluid supply circuit traverses a membrane in a sealed manner.

18. A unit according to claim 16, further comprising leak detection means, placed close to the external surface of the sample in the test zone and configured to detect any leak of fluid delivered via the second supply circuit at the periphery of the sample.

19. A unit according to claim 16, wherein the fluid moving in the second pressure means is a gas.

20. A unit according to claim 1, wherein the third pressure means comprises a third fluid supply circuit configured to supply each zone of action with fluid so as to exert the selected second internal pressure on the sample.

21. A unit according to claim 20, wherein the fluid of the third pressure means is a pressurized liquid.

22. A unit according to claim 20, further comprising a routing device connected to the first and third fluid supply circuits, and a pump coupled to the routing device.

23. A unit according to claim 14, wherein the support of the packer is a tube forming a hollow central conduit defining a portion of the third fluid supply circuit and comprising two opposed ends at least one of which opens into a zone of action to supply the tube with fluid.

24. A unit according to claim 1, comprising two plug members, installed at a distance from the two ends of the packer to define at least one zone of action so as to exert the selected second internal pressure on the sample at the zone of action.

25. A unit according to claim 23, wherein a portion of the first fluid supply circuit and/or a portion of the second fluid supply circuit is housed inside the central conduit.

26. A unit according to claim 1, further comprising at least one temperature sensor for installation at a selected region of the sample so as to deliver measurements representative of the temperature of the sample at the selected region.

27. A unit according to claim 1, further comprising at least one pressure sensor for installation at a selection region of the sample so as to deliver measurements representative of internal pressure of the sample at the selected region.

28. A unit according to claim 1, wherein the control means is configured to compare first results derived from at least some of first measurements with second results derived from at least some of second measurements, so as to authorize continuation of the test when the first results are compatible with the second results.

29. A unit according to claim 4, wherein the control means is configured to order the motor during a load test to drive the eccentric mass in rotation in accordance with a selected sequence of rotation rates so as to subject the sample to a selected sequence of vibratory excitations.

30. A method for mechanically loading a tubular sample comprising:
  introducing into the sample, at a test zone, at least one packer having a longitudinal extension greater than that of the test zone and including first and second and third pressure means;
  then locally varying a diameter of at least a first portion of the packer with the first pressure means so as to apply the packer against an internal surface of the sample, at the test zone, and to exert with the second pressure means a first selected internal pressure over a portion of the internal surface located at a second portion of the packer, and to attach at least one plug member to the sample at a distance from one end of the packer, to define a zone of action;
  then exerting a second selected internal pressure on the sample at the zone of action using the third pressure means.

31. A method according to claim 30, wherein at least one strain gauge is provided at at least one selected region of an external surface of the sample, so as to obtain first stress measurements representative of a stress state undergone by the sample at the selected region.

32. A method according to claim 30, wherein at least two strain gauges are provided at at least two selected regions of the external surface of the sample, so as to obtain first stress measurements representative of a stress state undergone by the sample at each of the two selected regions.

33. A method according to claim 30, wherein there is further provided two support means on which the sample is installed, and a rotary motor coupled to an excitation means, equipped with a device with an eccentric mass coupled to one end of the sample and defining an unbalanced mass, and the eccentric mass is driven in rotation using the motor at an adjustable rate, so as to subject the sample to a selected vibratory excitation, which is a function of the unbalanced mass, to deform the sample cyclically by bending.

34. A method according to claim 33, wherein at least one of the support means is placed at one vibration node of the sample.

35. A method according to claim 31, wherein during a preliminary reference step, an initial rotation rate of the motor is initially selected as a function of the amplitude of a stress which is to be undergone by the sample.

36. A method according to claim 35, wherein after the preliminary reference step, a rotation rate of the motor is adapted so that the amplitude of the bending stress undergone by the sample and represented by first measurements remains substantially constant.

37. A method according to claim 33, wherein there is provided at selected regions of the external surface of the sample at least one pair of accelerometers placed at 90° to each other and configured to deliver second measurements representative of a displacement undergone by the sample, and wherein a rotation rate of the motor is adapted as a function of last second measurements delivered by each pair of accelerometers, such that an amplitude of radial displacement by bending undergone by the sample at the selected region remains substantially constant.

38. A method according to claim 37, wherein there is provided at other selected regions of the external surface of the sample at least two other pairs of accelerometers, the accelerometers of each pair being placed at 90° to each other at other selected regions of the external surface of the sample and configured to deliver other second measurements representative of displacements undergone by the sample at the other selected regions, and wherein combinations of last second measurements are produced so as to adapt the rotation rate of the motor as a function of the combinations, such that the amplitude of the bending displacement undergone by the sample at the selected regions remains substantially constant.

39. A method according to claim 37, wherein at least the last second measurements delivered by at least one pair of accelerometers are compared with second reference measurements representative of an initial displacement amplitude corresponding to a desired bending displacement amplitude at the selected region, then a rotation rate of the motor is adapted as a function of the result of the comparison.

40. A method according to claim 39, wherein a relative difference between the displacement amplitude, represented by the last second measurements, and the desired bending displacement amplitude is determined, then the distance is compared with limits of a regulation tolerance interval, so as to adapt the rotation rate of the motor when the difference is outside the regulation interval.

41. A method according to claim 33, wherein each rotation imposed by the motor is detected.

42. A method according to claim 41, wherein the rotation rate of the motor is adapted each time a number of signals received is equal to a selected number.

43. A method according to claim 30, wherein at least one temperature sensor is provided, installed at a selected region of the sample so as to obtain measurements representative of the temperature of the sample at the selected region.

44. A method according to claim 30, wherein at least one pressure sensor is provided, installed at a selected region of the sample to obtain measurements representative of the internal pressure of the sample at the selected region.

45. A method according to claim 33, wherein during the loading test, the motor is ordered to drive the device with an eccentric mass in rotation in accordance with a selected sequence of rotation rates so as to subject the device to a selected sequence of vibratory excitations.

46. A method according to claim 30, wherein first stress results derived from at least some of first measurements are compared with second radial displacement results derived from at least some of second measurements to authorize the test to continue when the first results are compatible with the second results.

47. A method according to claim 30, wherein leak detection is carried out at the periphery of the sample at the test zone.

48. Use of a unit according to claim 1, to load samples selected from a group comprising i) a single tube, ii) a first tubular component defining a first tube and a second tubular component defining a second tube and connected to the first tube by welding, iii) a first tubular component defining a first tube provided with a male threading and a second tubular component defining a second tube provided with a female threading configured to cooperate with the male threading to constitute a threaded connection, iv) a first tubular component defining a first tube provided with a male threading, a second tubular component defining a second tube provided with a male threading, and a third tubular component defining a coupling provided with two female threadings configured to cooperate respectively with the male threadings to constitute a threaded connection, and v) a first tubular component defining a first tube, provided on its external surface with a male series of annular reliefs and grooves, and a second tubular component defining a second tube, provided on its internal surface with a female series of annular reliefs and grooves corresponding to the male series, configured to cooperate with the male series to constitute a connection between the two tubes.

* * * * *

UNITED STATES PATENT AND TRADEMARK OFFICE
CERTIFICATE OF CORRECTION

PATENT NO.       : 7,647,839 B2
APPLICATION NO.  : 11/816532
DATED            : January 19, 2010
INVENTOR(S)      : Didier David et al.

It is certified that error appears in the above-identified patent and that said Letters Patent is hereby corrected as shown below:

Column 16, line 46, change "$a'_n$" to -- $a'_n$ --;

line 47, change "$a'_n = a_n/\rho a$" to -- $a'_n = a_n/\rho a$ --;

line 56, delete the equation and insert $$-- \quad \Delta a = \frac{\sin\left(\frac{\pi \Delta' f}{\Delta f}\right)}{\frac{\pi \Delta' f}{\Delta f}} \quad --$$

line 61, delete the equation and insert $$-- \quad u = \frac{a'_n}{(2\pi f)^2} \quad --$$

Column 18, line 9, after "satisfied" insert --at--.

Column 21, line 38, change "U.S. Pat. No." to -- US-A- --;

line 46, change "U.S. Pat. No." to -- US-A- --.

Signed and Sealed this

Eleventh Day of May, 2010

David J. Kappos
*Director of the United States Patent and Trademark Office*